United States Patent
Austin et al.

(10) Patent No.: US 8,281,737 B2
(45) Date of Patent: Oct. 9, 2012

(54) COATED MEDICAL DEVICE AND METHOD FOR MANUFACTURING THE SAME

(75) Inventors: Michael Austin, Tuam (IE); Don Robinson, Framingham, MA (US); Dennis R. Boulais, Danielson, CT (US); Praveen Kulkarni, Worcester, MA (US); Toby Freyman, Waltham, MA (US); Samuel J. Epstein, Watertown, MA (US); Wendy Naimark, Cambridge, MA (US); Marlene Schwarz, Auburndale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1466 days.

(21) Appl. No.: 10/797,704

(22) Filed: Mar. 9, 2004

(65) Prior Publication Data

US 2005/0015142 A1   Jan. 20, 2005

(51) Int. Cl.
    *B05D 1/08* (2006.01)
(52) U.S. Cl. ......... 118/261; 118/203; 118/249; 118/642
(58) Field of Classification Search ................. 118/249, 118/261, 203, 642, 63, DIG. 3, 216, 255; 427/2.24, 2.25, 428.15
    See application file for complete search history.

(56) References Cited

U.S. PATENT DOCUMENTS

| 364,873 | A | * | 6/1887 | Underwood | 427/285 |
|---|---|---|---|---|---|
| 792,394 | A | * | 6/1905 | Buchanan | 118/69 |
| 2,842,092 | A | * | 7/1958 | Pomper | 118/248 |
| 3,867,315 | A | * | 2/1975 | Tigner et al. | 252/512 |
| 4,229,838 | A | | 10/1980 | Mano | |
| 5,464,650 | A | | 11/1995 | Berg et al. | |
| 5,500,013 | A | | 3/1996 | Buscemi et al. | |
| 5,679,400 | A | | 10/1997 | Tuch | |
| 5,837,008 | A | | 11/1998 | Berg et al. | |
| 5,843,172 | A | | 12/1998 | Yan | |
| 6,071,305 | A | | 6/2000 | Brown et al. | |
| 6,096,070 | A | | 8/2000 | Ragheb et al. | |
| 6,111,345 | A | * | 8/2000 | Shibata et al. | 313/141 |
| 6,240,616 | B1 | | 6/2001 | Yan | |
| 6,314,880 | B1 | | 11/2001 | Lampinski | |
| 6,365,149 | B2 | | 4/2002 | Vyakarnam et al. | |
| 6,379,381 | B1 | | 4/2002 | Hossainy et al. | |
| 6,395,326 | B1 | | 5/2002 | Castro et al. | |

(Continued)

FOREIGN PATENT DOCUMENTS

JP   11-111423   *   4/1999

(Continued)

OTHER PUBLICATIONS

Kirk Othmer, Encyclopedia of Chemical Technology, 3rd Edition, vol. 19, "Radiation Curing", pp. 607-624 (1982).*

(Continued)

*Primary Examiner* — Laura Edwards
(74) *Attorney, Agent, or Firm* — Vidas, Arrett & Steinkraus

(57) ABSTRACT

The medical device of the invention comprises a surface comprising at least one outermost portion and a plurality of depressions. The depressions occupy at least about 80% of the surface area of the surface. The depressions contain a coating material that preferably comprises a biologically active material and/or polymer, and the outermost portion is substantially free of any coating material. The invention is also directed to a method for manufacturing a medical device. The method comprises applying a coating material to the surface of the medical device by using at least one roller.

16 Claims, 19 Drawing Sheets

U.S. PATENT DOCUMENTS

| | | |
|---|---|---|
| 6,660,034 B1 | 12/2003 | Mandrusov et al. |
| 6,926,919 B1 | 8/2005 | Hossainy et al. |
| 6,971,813 B2 * | 12/2005 | Shekalim et al. ............. 401/208 |
| 6,984,411 B2 | 1/2006 | Palasis et al. |
| 6,986,899 B2 | 1/2006 | Hossainy et al. |
| 7,144,419 B2 | 12/2006 | Cheng et al. |
| 7,175,874 B1 * | 2/2007 | Pacetti ......................... 427/2.25 |
| 2001/0008649 A1 * | 7/2001 | Layrolle et al. ............. 427/2.24 |
| 2001/0029660 A1 | 10/2001 | Johnson |
| 2003/0105512 A1 | 6/2003 | Kanesaka |
| 2005/0074544 A1 * | 4/2005 | Pacetti et al. ................. 427/2.1 |
| 2005/0100654 A1 | 5/2005 | Su et al. |
| 2005/0106206 A1 | 5/2005 | Herweck et al. |
| 2006/0112536 A1 | 6/2006 | Herweck et al. |

FOREIGN PATENT DOCUMENTS

| | | |
|---|---|---|
| WO | WO 98/23228 | 6/1998 |

OTHER PUBLICATIONS

"Coating Techniques", http://www.ferron-magnetic.co.uk, Jan. 9, 2002.

"Micro Gravure™", http://www.yasui.com, Jan. 9, 2002.

* cited by examiner

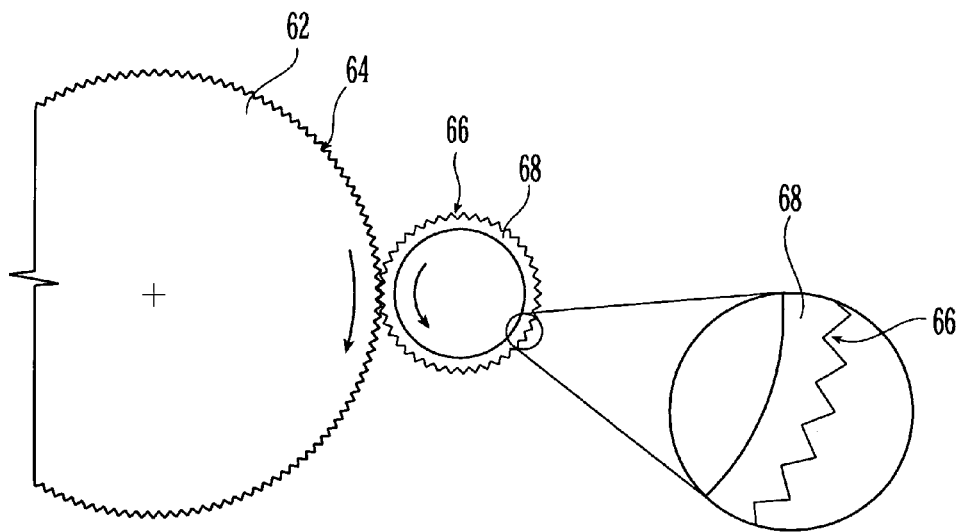
*Fig. 6A*  *Fig. 6B*
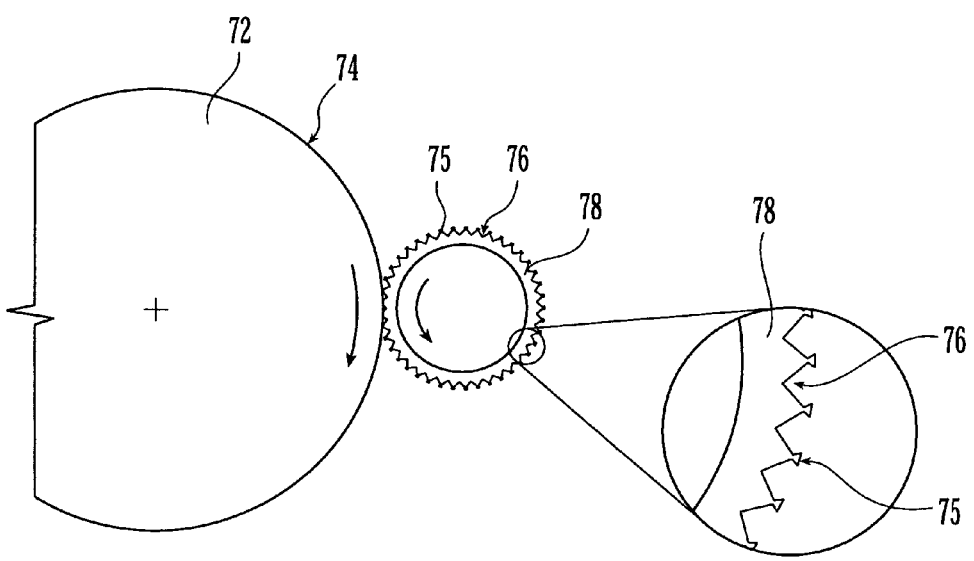
*Fig. 7A*  *Fig. 7B*

COATED MEDICAL DEVICE AND METHOD FOR MANUFACTURING THE SAME

FIELD OF THE INVENTION

This invention relates generally to medical devices having a coating. The medical device is capable of delivering a biologically active material to a desired location within the body of a patient. More particularly, the invention is directed to medical devices having a surface comprising at least one outermost portion and a plurality of depressions. The depressions contain a coating material preferably comprising a biologically active material, and the outermost portions are substantially free of any coating material. The invention is also directed to a method and system for manufacturing a coated medical device involving the use of roller(s).

BACKGROUND OF THE INVENTION

It has been proposed that a variety of medical conditions can be treated by introducing an insertable or implantable medical device having a coating for release of a biologically active material. For example, various types of drug-coated stents have been proposed for localized delivery of drugs to a body lumen. See U.S. Pat. No. 6,099,562 to Ding et al.

However, the coatings for a medical device can exhibit problems of cracking especially when the device is exposed to harsh conditions, such as low temperatures and/or mechanical deformations. For example, a self-expanding stent must be contracted and loaded into a delivery sheath before delivering into a patient's body. To contract a self-expanding stent made of a shape-memory alloy, it must be chilled to be thermally induced into the Martenstic phase, in which the shape-memory alloy can be plastically deformed. In practice, the self-expanding stent is chilled to about −80° to −100° C. and then warmed to about −60° to −20° C. when it is contracted. However, the processing temperature about −60° to −20° C. is usually the same as or lower than the glass transition temperatures of many polymers. Therefore, when chilled to these temperatures, a polymer coating on the stent is in a condition like glass and particularly vulnerable to stress-cracking when the device is processed.

The risk of cracking the coating is particularly high in certain parts of the coated stent, such as the apex regions of a zigzag strut configuration where the surface of the strut is greatly deformed by contraction of the stent as shown in FIGS. 1, 1a and 2. FIG. 1 shows a schematic view of a portion of a stent 10 having struts 11 in its expanded state. The apex regions of the zigzag strut configuration 12 are magnified in FIG. 1a. FIG. 2 shows a schematic view of the same apex regions 12 when the stent is in its contracted state and the cracks 13 in the coating that may occur at the apex regions. Cracks in the coating are undesirable because they can cause the coating to flake or separate from the coated surface of the device while the coated medical device is inside the body of a patient. Such separated or loose pieces of coating can cause emboli. Hence, there is a need for a coated medical device wherein a risk of cracks in the coating is reduced.

Furthermore, when a medical device such as a stent is delivered to the implantation site, the coated surface of the medical device is often covered by a sheath to prevent the coating from being removed before the medical device is inserted and appropriately located inside the body. Also, if the coated surface of the medical device is self-expanding, a sheath is used to contract the portion so that the device can be inserted, such as in the case of a self-expanding stent. However, the sheath is likely to contact the coating located on the outermost portion of the coated surface. The coating material at such outermost portion may adhere to the sheath. When the sheath is withdrawn, the adhered coating may be torn or removed from the coated device. Therefore, there is a need for a coated medical device that avoids such undesired tearing of the coating.

Also, the conventional methods for coating medical devices require encapsulating the device or coating entire surfaces of the device. However, in many medical devices, not all of the surfaces or the entirety of the surfaces of the medical device need to be coated. For instance, in medical devices having a tubular portion, such as a vascular stent, the inner surface of the tubular portion does not have to be coated with a coating containing a biologically active material that is used to treat only the body lumen wall that contacts the outer surface of the stent. This is because the inner surface of the stent does not come in contact with body-lumen wall and does not apply the biologically active material to the body-lumen wall. When all the surfaces of a medical device such as a stent, including surfaces that are not directly in contact with the body tissue of a patient, are coated with a composition comprising a biologically active material, more biologically active material is used than is needed. Thus, the patient may receive unnecessary exposure to the material. Also, manufacturing costs for the medical device may be needlessly increased by including unnecessary amounts of the biologically active material in the medical device.

Moreover, if the medical device is an expandable stent, the coating on the sides of the struts may adhere to each other when the stent is placed in its contracted state. When the stent is expanded, the adhered coating may be removed from the struts. In addition, if the medical device is a balloon expandable stent, the coating on the inner surface of the stent has higher risk of damage because it directly contacts the balloon and is pressed by a balloon. Such damage is undesirable because the damaged coating may separate from the device while the device is inserted in a patient. Accordingly, there is a need for a method that can coat only the outer surface of a medical device or the surface that directly contacts the body tissue to be treated.

SUMMARY OF THE INVENTION

The present invention is directed to a medical device comprising a structure. The structure has a thickness and a surface. The surface of the structure comprises at least one outermost portion and a plurality of depressions. These depressions occupy at least about 80% of the surface area of the surface. Also, at least one of the depressions contain a coating material. Preferably, a majority of the depressions contain coating material. The outermost portion of the surface is substantially free of any coating material. This coating material can contain a biologically active material and/or a polymer.

Furthermore, the present invention relates to a method for manufacturing a medical device. In this method, a medical device having a surface is obtained. The surface of the medical device comprises at least one outermost portion and a plurality of depressions. The depressions occupy at least about 80% of the surface area of the surface. A coating material is applied to the surface of the medical device in a manner such that the outermost portion of the surface is substantially free of any coating material and the coating material is present in at least one of the depressions. The outermost portion may be made substantially free of the coating material by removing the coating material from the outermost portion.

In addition, another embodiment of the invention involves a system and a method for manufacturing a medical device having at least a tubular portion, wherein the tubular portion has a surface. In this system a coating material is applied on a surface of a first roller. The coating material is then transferred from the first roller surface to the surface of the tubular structure. Also, if there is an excess amount of the coating material on the first roller surface, it can be removed, e.g., by a doctor blade, before the coating material is transferred to the surface of the tubular portion. Additionally, the method can involve a second roller. The coating material on the first roller surface is transferred onto a surface of a second roller. Then, the coating material is transferred from the second roller surface to the outer surface of the tubular portion.

The present invention also pertains to a system for coating a medical device having a tubular portion with an outer surface. The system comprises a coating material source containing a coating material. The system also includes a roller having a surface, in which the roller is situated relative to the coating material source so that the coating material in the coating source can be transferred to the roller surface. Also, the roller is situated relative to the outer surface of the tubular portion so that the roller surface can transfer the coating material transferred to the roller surface onto the outer surface of the tubular portion. The system can further include a reservoir that continuously supplies the coating material source with coating material. In addition, the surface of the roller can comprise a plurality of grooves.

In another embodiment, the system for coating a medical device comprises a coating material source containing a coating material, a first roller having a surface and a second roller having a surface. The first roller is situated relative to the coating material source so that the coating material in the coating material source can be transferred to the first roller surface. The first roller and second roller are situated relative to each other so that the first roller can transfer the coating material transferred to the first roller surface to the second roller surface. The second roller is situated relative to the tubular portion so that the second roller can transfer the coating material transferred to the second roller surface to the outer surface of the tubular portion. The surface of the second roller can be rougher than the surface of the first roller. Preferably, the first roller contacts the surface of the second roller and the surface of the second roller contacts the outer surface of the tubular portion. Also the system can include a mechanism for removing excess coating material from the surface of the first roller. Furthermore, the system can include an energy source for converting the coating material applied to the outer surface of the tubular portion into a coating.

In yet another embodiment, the system comprises a coating material source containing a coating material; a first roller having a surface; a second roller having a surface; a third roller having a surface; and a flexible webbing material position around the second and third rollers. The first roller is situated relative to the coating material source so that the coating material can be transferred to the first roller surface. The first roller and webbing are situated relative to each other so that the first roller can transfer the coating material transferred to the first roller surface to the webbing. Additionally, the webbing is situated relative to the tubular portion so that the webbing can transfer the coating material transferred to the webbing to the outer surface of the tubular portion. Preferably, the webbing contacts the outer surface of the tubular portion.

The present invention is also directed to a system for coating a medical device having a tubular portion with an outer surface in which the system comprises a roller having a surface and an applicator for applying an adhesion protein to the roller surface. The roller is situated relative to the tubular portion so that the roller can transfer the adhesion protein to the outer surface. The outer surface is exposed to a cell suspension and the adhesion protein can be transferred to the outer surface as the outer surface is simultaneously exposed to the cell suspension.

Moreover, the present invention is directed to a lithographic method for coating a medical device having a tubular portion with an outer surface. The method comprises providing a layer of an unsolidified gel. A crosslinking agent is applied onto the outer surface of the tubular portion. The crosslinking agent is transferred from the outer surface of the tubular portion to the gel layer by rolling the tubular portion over the gel layer to form a crosslinked, planar replica of the outer surface onto the unsolidified gel to crosslink the unsolidified gel. An adhesive material is applied onto the outer surface of the tubular portion. The tubular portion is rolled over the gel in the same manner as the first time the tubular portion was rolled over the gel so that the crosslinked planar replica is aligned with and attaches to the outer surface of the tubular portion.

BRIEF DESCRIPTION OF THE DRAWINGS

FIG. 6A is a schematic illustration of a pressure-rolling method for making depressions on a surface of a medical device.

FIG. 6B depicts a magnified cross-sectional view of the surface of the medical device shown in FIG. 6A.

FIG. 7A is a schematic illustration of a method for forming outermost portions of the surface that extend over the depression in the surface of a medical device.

FIG. 7B depicts a magnified cross-sectional view of the surface of the medical device in FIG. 7A.

DETAILED DESCRIPTION OF THE INVENTION

1. Suitable Medical Devices

Figures 1, 1A:
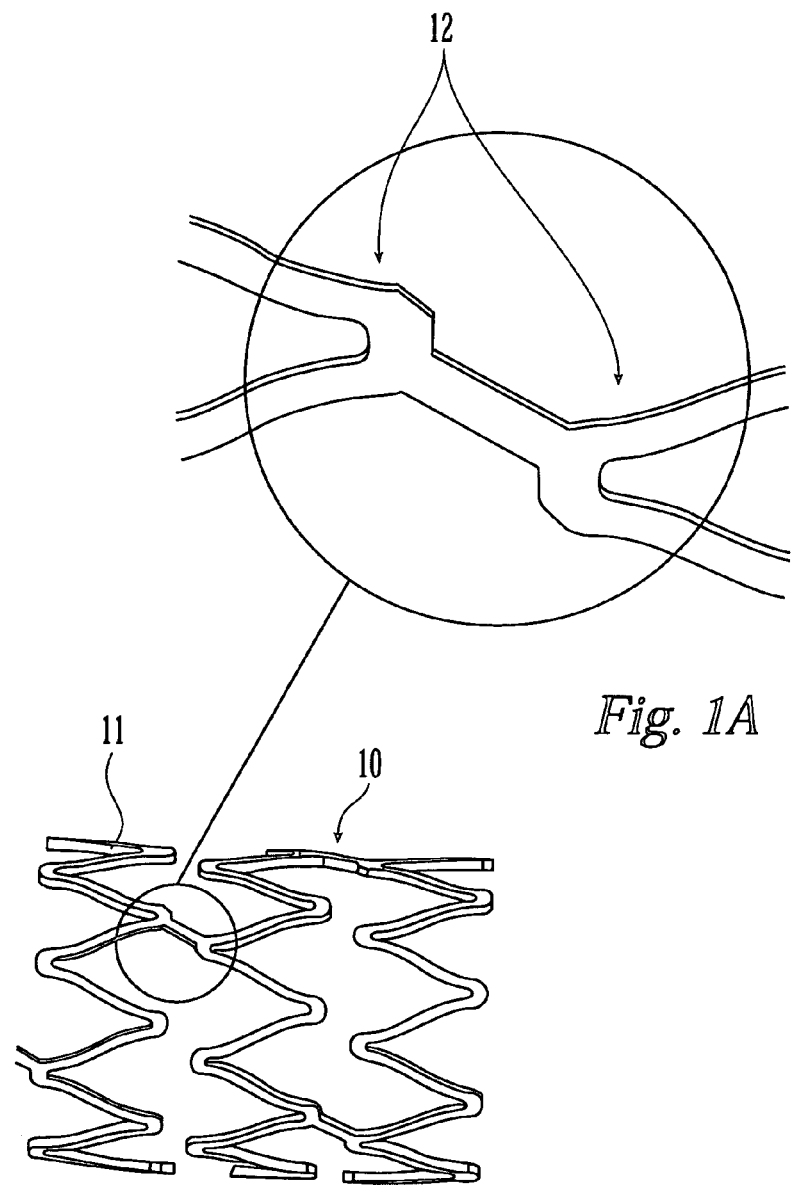
FIG. 1 schematically depicts a portion of a stent comprising struts in its expanded state.
FIG. 1a is a magnified view of the link-connected apex regions of the stent struts depicted in FIG. 1.

The medical devices of the present invention can be inserted and may be implanted into the body of a patient. The medical devices suitable for the present invention include, but are not limited to, stents, surgical staples, catheters, such as central venous catheters and arterial catheters, guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, and extra-corporeal devices such as blood oxygenators, blood filters, hemodialysis units, hemoperfusion units and plasmapheresis units.

Medical devices of the present invention include those that have a tubular or cylindrical-like portion. The tubular portion of the medical device need not to be completely cylindrical. For instance, the cross-section of the tubular portion can be any shape, such as rectangle, a triangle, etc., not just a circle. Such devices include, without limitation, stents and grafts. A bifurcated stent is also included among the medical devices which can be fabricated by the method of the present invention.

Medical devices which are particularly suitable for the present invention include any kind of stent for medical purposes which is known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

The medical devices suitable for the present invention may be fabricated from metallic and/or polymeric materials. Metallic material is more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646. Suitable polymeric materials include, without limitation, polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

In embodiments of the present invention, the insertable or implantable portion of the medical device of the present invention has a thickness and a surface that comprises at least one outermost portion and a plurality of depressions. The term "depression" refers to an indentation, receptacle or groove in the surface. The depression can have any cross-sectional configuration or shape. The term "outermost portion of the surface" refers to the highest portion of the surface of the medical device or that portion of the device surface that is most likely to first contact body tissue upon insertion of the device. The depressions occupy at least about 80% of the surface area of the surface upon which the coating is disposed, preferably at least about 90% of the surface area of the surface. Having the depressions occupy at least about 80% of the surface area allows the administration of high amounts of a drug or biologically active material. Also, by having the depressions occupy at least about 80% of the surface area allows for the delivery of a drug or biologically active material evenly over most of the surface area.

Figure 3A:
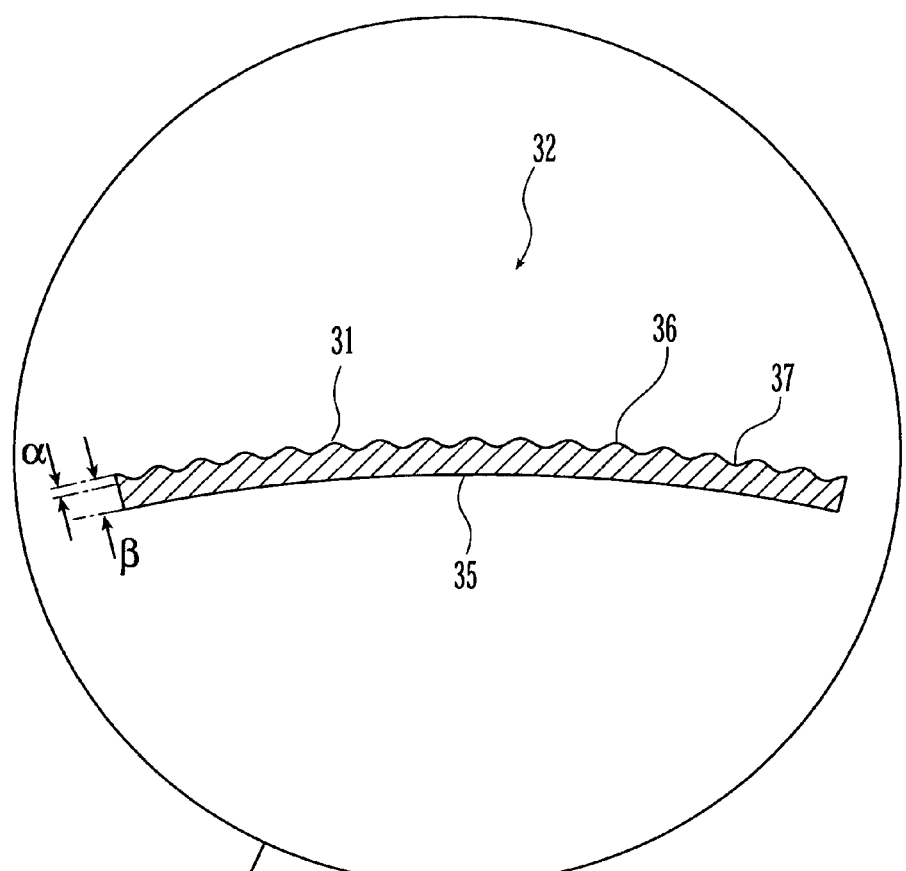
FIG. 3a depicts a magnified view of a cross-section of the struts of the stent depicted in FIG. 3.
Figure 3:
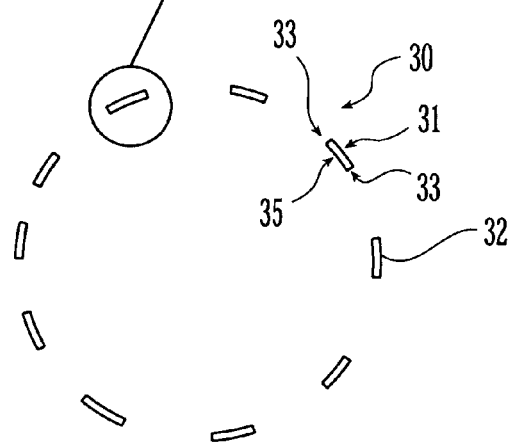
FIG. 3 depicts a cross-sectional view of a stent in which a surface of the stent struts are comprised of a plurality of outermost portions and a plurality of depressions.

FIG. 3 shows a cross-sectional view of a stent 30 having struts 32. FIG. 3a is a magnified view of a cross-section of one of the struts 32. The strut has an inner surface 35, outer surface 31 and side surfaces 33. The outer surface 31 comprises outermost portions 36 and depressions 37. In the present invention it is preferred that the depressions have a maximum depth $\alpha$ i.e., deepest part, of about 4% to about 20% of the maximum thickness $\beta$ of the strut 32 or structure of the medical device (see FIG. 3a). More preferably, the maximum depth of the depressions is about 6% to about 10%, of the maximum thickness of the strut or structure 32 of the medical device.

Figure 4:
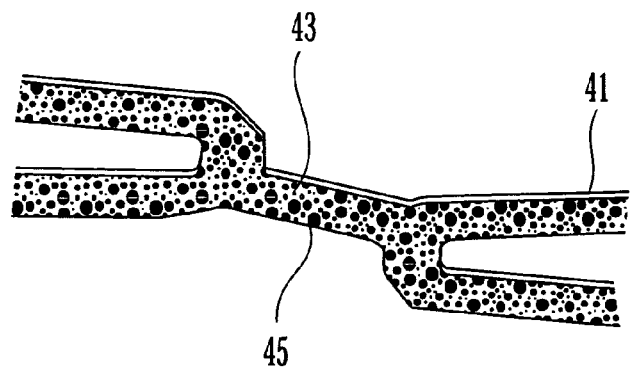
FIG. 4 depicts a top view of a stent strut having a surface comprised of outermost portions and a plurality of depressions.
Figure 5A:
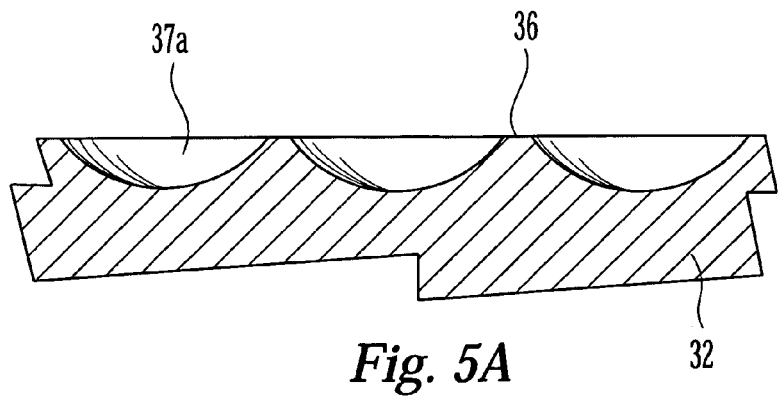
FIGS. 5A, 5B, 5C and 5D depict cross-sectional views of depressions in which the depressions have various cross-sectional configurations.
Figure 5B:
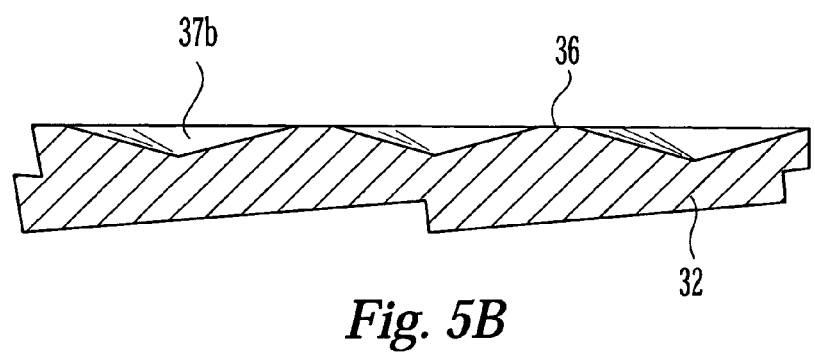
Figure 5C:
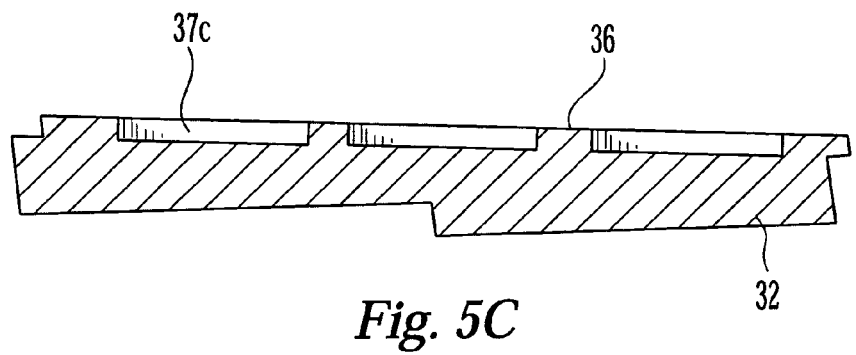
Figure 5D:
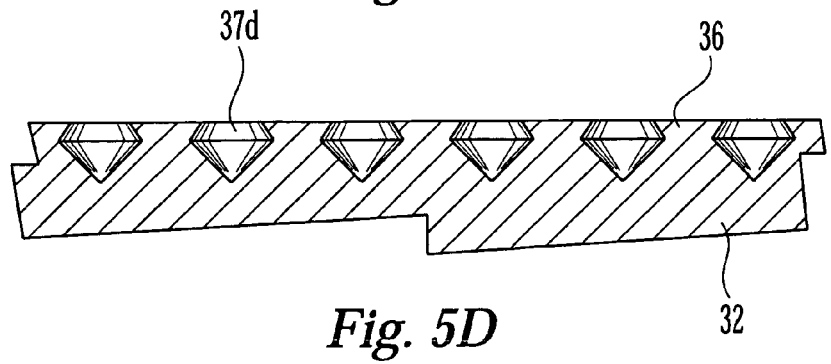

FIG. 4 shows a top view of a portion of a stent strut 41 having a surface having outermost portions 43 and depressions 45. As shown in this figure the plurality of depressions cover at least 80% of the surface area of the surface of the strut 41. The depression can have widths or diameters that are uniform or the depressions can have varying widths or diameters.

Furthermore, examples of suitable cross-sectional configurations or shapes of the depressions are shown in FIGS. 5A-5D. Such suitable cross-sectional shapes include, but are not limited to, a truncated circle 37a, a triangle 37b, a rectangle or square 37c and a truncated diamond 37d. Preferably, the depression 37 in the surface of the strut 32 should be separated by an outermost portion 36. Also, preferably, the average width or diameter of the depression is about 80 μm to about 180 μm. The depression can all have the same cross-sectional shapes or the shape can vary from depression to depression.

Figure 2:
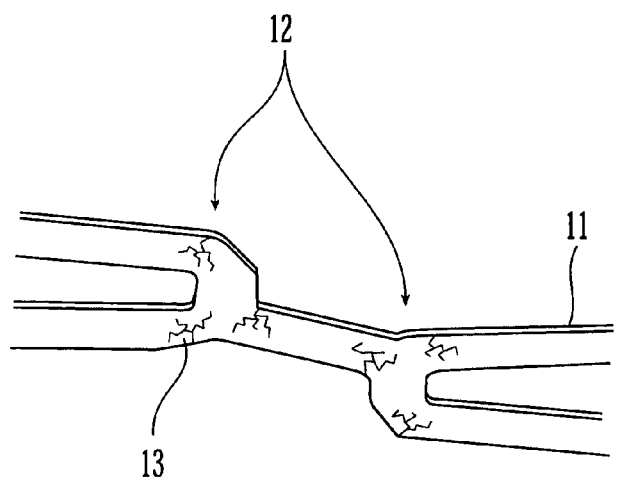
FIG. 2 schematically depicts the same link-connected apex regions as in FIG. 1 when the stent is in its contracted state.

The depressions can be situated in a regular pattern, such as in a row, on the surface of the medical device as shown FIGS. 5A-5D. But the depressions can also be arranged in any way, either in a regular pattern or in a irregular manner. Also, the depressions do not have to be deposed evenly on the entire surface of the medical device. In one embodiment, the density of the depressions that are disposed on the surface of the medical device is greater in areas where cracking of the coating is likely to occur, such as apex regions 12 as shown in FIG. 2. In another embodiment, the depressions are more densely deposed on the surface in areas where a stronger release of the biologically active material is desired. In yet another embodiment, the depressions are localized in one or more areas on the surface, and other areas of the device do not comprise depressions.

The depressions in the device surface can be formed by chemical etching, photo-etching, high-velocity particle impact ("blast methods"), pressure-rolling or laser ablation. The blast methods include a method wherein various high-velocity and hard particles are blasted to a surface of the medical device. The pressure-rolling method involves impressing a hard die onto a flat perform surface of the medical device. The die surface being etched or machined to possess a number of small projections. Under pressure these projections indent the preform surface with suitable depressions. For example, FIG. 6A is a schematic illustration of a pressure-rolling method for making depressions 66 on a surface of a medical device 68. A roller 62 having small projections 64 on its outer surface is used as the hard die. The roller 62 is rotated, and the projections 64 of the roller 62 are impressed onto the surface of a tubular medical device 68 to create the depressions 66 on the surface of a part of a medical device, e.g., a strut. FIG. 6B depicts a magnified cross-sectional view of the medical device surface 68 having the depressions 66.

In another embodiment, the depressions can be modified after they are formed. For example, as shown in FIG. 7A, a roller 72 having a hard and polished outer surface 74 is rotated, and the surface 74 is pressed against the outermost portions of the surface of tubular medical device 78. FIG. 7B depicts a magnified cross-sectional view of the medical device surface 78 having deformed depressions 76. The outermost portions 75 are pressed or deformed so that the outermost portions 75 extend over the depressions 76. By doing so the width of an upper portion of the depressions is made smaller than the width of a lower portion of the depressions. Such configuration is desirable since it enhances the ability of the depressions to retain coating material. By varying the pressure with which the roller is impressed onto the medical surface, a desired degree of the deformation can be achieved.

2. Coating

In the present invention, a coating composition or material, which preferably contains a biologically active material, can be applied by any method to a surface of a medical device to form a coating. The method should apply the coating material in a manner such that the coating material is deposited in the depressions, and the outermost portions of the surface are substantially free of any coating material. More specifically, the outermost portions of the surface contain none or negligible amounts of any coating material.

Examples of suitable methods for applying the coating material are spraying, dipping, rolling, electrostatic deposition and all modem chemical ways of immobilization of bio-molecules to surfaces. One of the suitable methods of applying a coating material to the medical device is a rolling technique, which is explained in detail in section 3, infra. Also, in one embodiment of the present invention, more than one coating method can be used to make a medical device.

Furthermore, before applying the coating material, the surface of the medical device is optionally subjected to a pre-treatment, such as roughening, oxidizing, sputtering, plasma-deposition or priming in embodiments where the surface to be coated does not comprise depressions. Sputtering is a deposition of atoms on the surface by removing the atom from a cathode by positive ion bombardment through a gas discharge. Also, exposing the surface of the device to a primer is a possible method of pre-treatment.

A coated medical device surface in which the coating material is contained in the depressions and in which the outermost portions of the device surface are substantially free of any coating material provides several advantages. First, this coating reduces the risk that the coating will crack when the coated portion of the medical device is subjected to mechanical stress, such as when a stent is expanded and contracted. In the coating of the present invention, coating material is not present on the entire surface of the medical device that is coated. The coating material is present in the depressions of the surface but substantially absent from the outermost portions of the device surface. Hence, the coating formed on the device surface is discontinuous because the coating material contained in a depression is generally not connected by coating material to the coating material contained in another depression since these depressions are separated by an outermost portion that is substantially free of such coating material. When a mechanical stress is applied to the coated device surface, the likelihood that the stress is transmitted throughout the coating on the device surface is greatly reduced because of the discontinuous nature of the coating. Transmission of compressive, tensile or shear stresses throughout the coating is blocked because the coating materials in the depressions are isolated from each other. By preventing transmission of these stresses throughout the coating, cracking of the coating due to these stresses is reduced. For example, the risk that the coating in the apex regions 12 of struts 11 of a self-expanding stent 10 will crack as shown in FIG. 2, even if the stent is contracted at a temperature lower than the glass transition temperature of the coating material, is reduced.

In addition, the possibility that the coating is inadvertently or undesirably removed or abraded from the coated device surface is greatly reduced in the present invention. For example, when the medical device is a self-expanding stent, a sheath is usually placed over the stent to contact the stent during delivery of the stent to the implantation site. The outermost portion of the coated surface generally comes in contact with the sheath. If coating material is placed over the outermost portions, such coating material can adhere to the sheath. When the sheath is removed, the coating on the device surface can be undesirably torn or removed from the surface. However, in the present invention, because the outermost portions of the device surface, which contact the sheath are substantially free of coating material, the chances that the coating on the device surface will be damaged will be reduced. Since the outermost portions are substantially free of coating material, there will be no adhering of such coating material to the sheath and no undesired removal of coating when the sheath is removed. Thus, the coating will not be damaged when the coated self-expanding stent is loaded in a delivery sheath and exposed to continuous radial pressure against the inner wall of the sheath, even if the stent is loaded in the sheath for long period.

One way to ensure that the coating material is applied to the surface in a manner such that the outermost portions are substantially free of any coating material is to remove such coating material from those outermost portions. In one embodiment, the coating material is removed using a doctor blade. The doctor blade is for example a flexible blade that scrapes the coating material from the outermost portion of the surface of the medical device. Furthermore, a small roller engaged in roller-contact with the surface of the device can be used to ensure that the coating material is applied to the surface so that the outermost portions are substantially free of coating material. When the small roller and the surface of the medical device are rotated, excess coating material is squeezed off the outermost surface of the medical device. Preferably, the small roller has a rubber surface. Also, the small roller can have a groove into which an O-ring can be placed. When the small roller is engaged in roller-contact with the surface of the device, the O-ring can function as a modified doctor blade or wipe strip to remove the coating material from the outermost portion of the device surface.

In one embodiment, the medical device has a tubular portion where the outer surface is to be coated. The doctor blade is put in contact with surface of the tubular portion which has been coated by the coating material. This portion is then rotated and the doctor blade removes coating material from the outermost portions of the surface. To maintain an appropriate pressure of the doctor blade on the surface, the doctor blade may be spring-loaded against the surface of the medical device. After the removal, the outermost portions of the surface are substantially free of the coating material. The term "substantially free of a coating material" means that only a very small residual amount of coating material remains on the outermost portions of the surface or that the outermost portions are covered with no coating material. After the coating material is applied to the device surface and is removed from the outermost portions, the solvent evaporates to leave a polymeric coating material in the depressions.

Figure 7C:
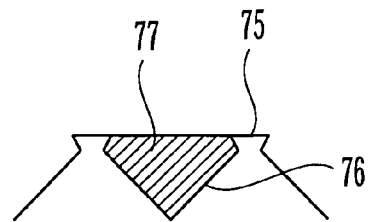
FIGS. 7C, 7D and 7E show depressions containing coating material.
Figure 7D:
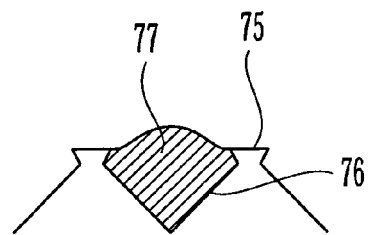

Also, as shown in FIG. 7C, it is preferable that the coating material 77 contained in the depressions 76 be contained entirely within the depression 76. As seen in this figure, the coating material 70 is confined within the depression 76 and the outermost portions of the surface 75 are substantially free of coating material. However, the coating material 77 can also extend beyond or above the depression 76 as shown in FIG. 7D, as long as the outermost portions 75 of the surface remain substantially free of coating material.

Figure 7E:
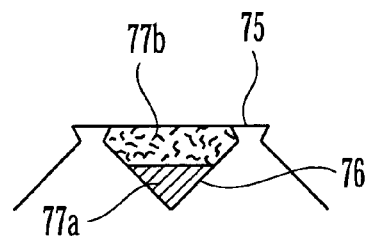

The coating material present in the depressions may comprise more than one layer. For example, the coating can comprise a first layer and a second layer disposed over the first layer. FIG. 7E shows such an embodiment. The depression 76 contains a first layer of coating material 77a and a second layer of coating material 77b, which is disposed over the first layer 77a. The layers may contain the same or different biologically active materials. Alternatively, the first layer and the second layer may contain the same biologically active material but have different concentrations of this material. In another embodiment, either the first layer or the second layer may be free of biologically active material.

Coating compositions suitable for applying coating materials to the devices of the present invention preferably include a polymeric material and/or a biologically active material dispersed or dissolved in a solvent suitable for the medical device, which are known to the skilled artisan. The solvents used to prepare coating compositions include ones which can dissolve the polymeric material into solution or suspend the polymeric material and do not alter or adversely impact the therapeutic properties of the biologically active material employed. For example, useful solvents for silicone include tetrahydrofuran (THF), chloroform, toluene, acetone, isooctane, 1,1,1-trichloroethane, dichloromethane, and mixture thereof.

The polymeric material should be a material that is biocompatible and avoids irritation to body tissue. Preferably the polymeric materials used in the coating composition of the present invention are selected from the following: polyurethanes, silicones (e.g., polysiloxanes and substituted polysiloxanes), and polyesters. Also preferable as a polymeric material are styrene-isobutylene copolymers. Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

More preferably for medical devices which undergo mechanical challenges, e.g., expansion and contraction, the polymeric materials should be selected from elastomeric polymers such as silicones (e.g., polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition is capable of undergoing deformation under the yield point when the device is subjected to forces, stress or mechanical challenge.

The term "biologically active material" encompasses therapeutic agents, such as drugs, and also genetic materials and biological materials. The genetic materials mean DNA or RNA, including, without limitation, DNA/RNA encoding a useful protein intended to be inserted into a human body including viral vectors and non-viral vectors. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor $\alpha$ and $\beta$, platelet derived endothelial growth factor, platelet derived growth factor, tumor necrosis factor $\alpha$, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progentitor cells) stem cells (e.g., mesenchymal, hematopoietic, neuronal), pluripotent stem cells, fibroblasts, macrophage, and satellite cells.

Biologically active material also includes non-genetic therapeutic agents, such as:
  anti-thrombogenic agents such as heparin, heparin derivatives, urokinase, and PPack (dextrophenylalanine proline arginine chloromethylketone);
  anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives and cladribine;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promoters such as growth factors, Vascular Endothelial Growth Factors (FEGF, all types including VEGF-2), growth factor receptors, transcriptional activators, and translational promoters;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin, and rapamycin, angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

3. Coating System Comprising Roller(s)

The present invention also comprises a method and a system for manufacturing a medical device by applying a coating material to the surface of a tubular portion of the device using at least one roller. In the system, a first roller rotates through a coating material source to wet a surface of the first roller with the coating material. A doctor blade contacts the surface of the first roller to remove any excess amount of the coating material from the roller surface. Afterward, the coating material on the first roller surface is transferred to the surface of the tubular portion of the medical device.

The doctor blade is a flexible blade and may have a curved edge. It is used to make uniform the coating material on the surface of the first roller and also to control the thickness of the coating material on the surface of the roller by removing any excess amount of the coating material. To maintain an appropriate pressure of the doctor blade against the roller surface, the doctor blade may be spring-loaded. Also, the doctor blade can be used in conjunction with another roller, such as a metering roller to control the amount of coating material applied to the roller. Moreover, instead of or in addition to the doctor blade, an air source or air knife may be used to control the thickness or amount of coating material applied to the roller. For example, the high pressure air of the air knife or air source removes undesired amounts of the coating material from the roller.

The coating material source may be connected to a main reservoir, which contains the coating material. For instance, in the case of cell therapy coatings, the coating material source may be connected to a reservoir that is a fermentor for cells or cell culture reservoir, where cells are grown and/or transduced with a particular gene therapy. The coating material can circulate between the reservoir and the coating material source. A valve system can be used to control flow between the coating material source and the cell culture reservoir. Sensor systems based on optical density or fluorescence spectroscopy to assess particular protein products generated by the cells can be used to trigger the valve.

Furthermore, the main reservoir can be thermally jacketed to control the temperature. By controlling the temperature, temperature sensitive hydrogels (i.e., poloxamers which are soluble at low temperatures and gel at elevated temperatures, can be coated onto the device. In the case of cell therapy coatings, temperature control can be used to preserve cell viability and/or trigger cell processes (i.e., induce heat shock proteins).

In one embodiment, the outer surface of the tubular portion of the medical device contacts the surface of the rotating first roller. The tubular portion of the medical device is situated parallel to the first roller and may rotate in a direction same as or opposite to the rotation of the first roller. Preferably, a tubular portion of the medical device to be coated is mounted on a mandrel or a tube which can be thermally jacketed. When the portion of the medical device is expandable, such as in a self-expanding stent or a balloon expandable stent, the diameter of the mandrel or tube may be greater, preferably slightly greater, than the diameter of the tubular portion in its normally expanded state.

Figure 8A:
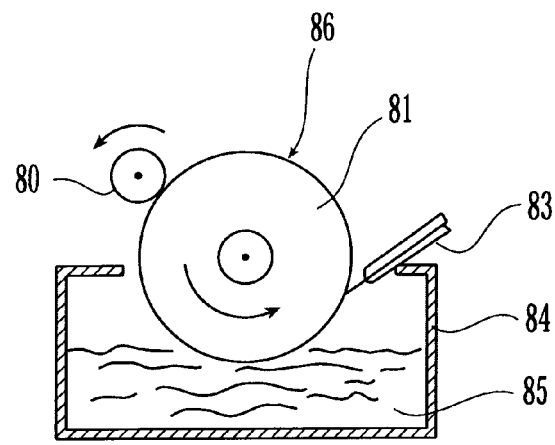
FIGS. 8A, 8B and 8C are schematic illustrations of embodiments of a coating system having a roller.
Figure 8B:
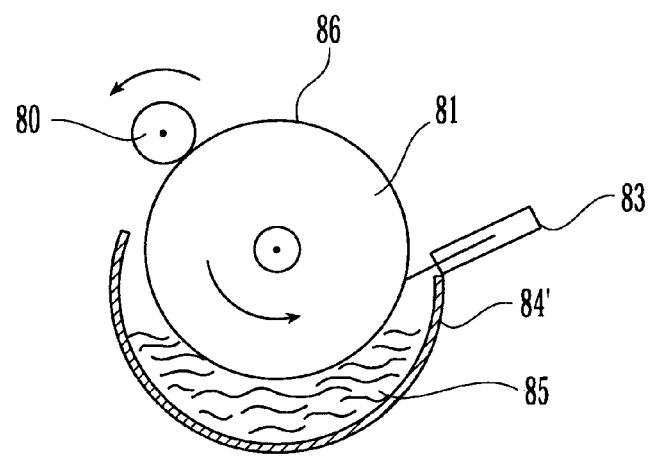

FIGS. 8A and 8B schematically depict a system of the present invention. A first roller 81 is situated relative to the coating material source so that coating material can be transferred onto the roller surface. Preferably, the roller surface is in contact with the coating material in the coating material source. The roller 81 rotates and the coating material 85 maintained in the coating material source 84 or 84' is transferred to the surface of the first roller 86. In FIG. 8A, the coating material source is contained in a box-like container, while in FIG. 8B, the coating material source is contained in a rounded container. The doctor blade 83, which is flexible and preferably having a curved edge, contacts the surface of the first roller 86 to ensure that the coating material is uniformly placed on the roller surface 86 and to remove any excess amount of the coating material 85 from the roller surface 86. The doctor blade can have a beveled or square edge. The tubular portion of the medical device 80 is situated relative to the first roller so that the first roller can transfer the coating material to the outer surface of the tubular portion. The medical device can rotate reversely relative to the first roller 81. The device's outer surface should be close to, but not in actual contact with, the roller. It should however be in sufficiently close proximity to be in rolling contact with the thin film of fluid coating material on the roller.

In another embodiment, a number of systems, each comprising roller(s) and coating material source(s) can be arranged in serial fashion. The mandrel, upon which the medical device is mounted, moves across each system, allowing the outer surface of the device to be coated by the various types of coating materials of each system. In this way, different layers of coating material can be applied to the device surface. The layers can contain the same or different compositions.

Figure 8C:
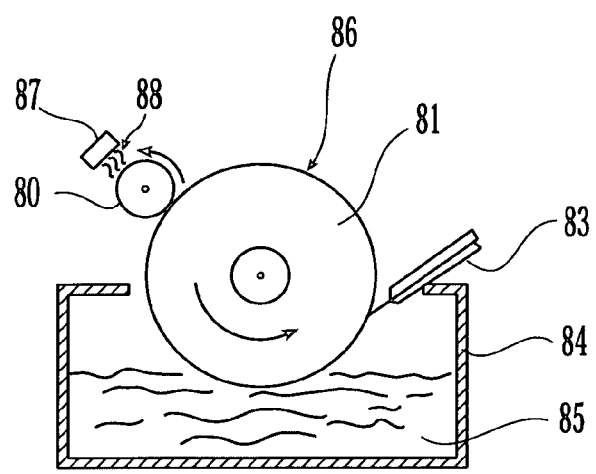

In addition as shown in FIG. 8C, the system can also include an energy source 87 for facilitating the formation of a coating on the surface of a medical device surface 80. The energy source 87 emits energy 88 such as heat to help cure the coating material 85 applied to the device surface 80 or removal of solvents from the coating material applied to the device. Preferably, only a small part of the device surface is exposed to the energy source at a given time. By limiting the area of the device surface that is exposed to the energy source, such as a heater, the environmental temperature of the area surrounding the system can remain low. Suitable energy sources include heaters, ultraviolet light and vacuum dryers, heating lamps, bone-dry air blowers, preheated gases such as air or nitrogen, as well as ceramic fibre, multi-cell, strip, cast-in, fan, cable or cartridge type heaters. When an ultraviolet source is used prepolymers or polymers that may be present in the coating materials can be crosslinked or polymerized.

In other embodiments, the system uses more than one roller. For example, a second roller is used in addition to the first roller. After the coating material on the surface of the first roller is made uniform by the doctor blade, the coating material on the first roller surface is transferred to the surface of the second roller. The second roller can be situated parallel to the first roller and may rotate in a direction same as or opposite to the rotation of the first roller. In one embodiment, another doctor blade may be used for controlling the uniformity and thickness of the coating material applied to the surface of the second roller. Afterward, the second roller transfers the coating material to the outer surface of the medical device. In other embodiments, the distance between the rollers can be used to control the thickness of the coating material applied to the surface of the device. In this way, one of the rollers can function as a metering roller.

Figure 9A:
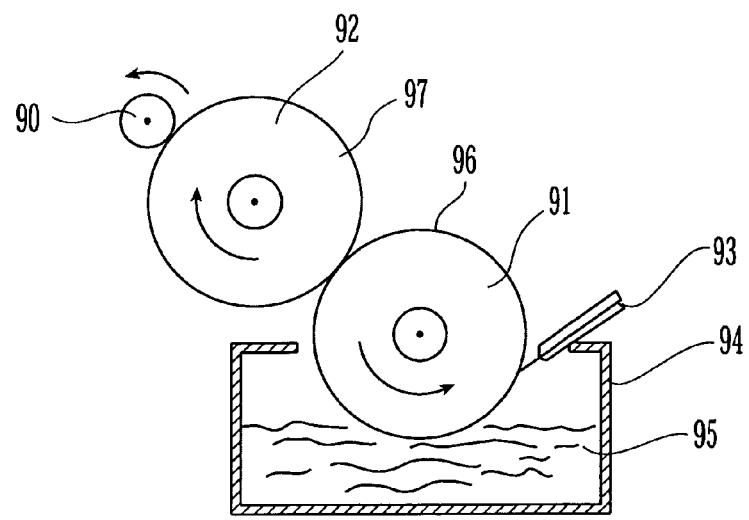
FIGS. 9A, 9B, 9C, 9D and 9E are schematic illustrations of embodiments of a coating system having two rollers.
Figure 9B:
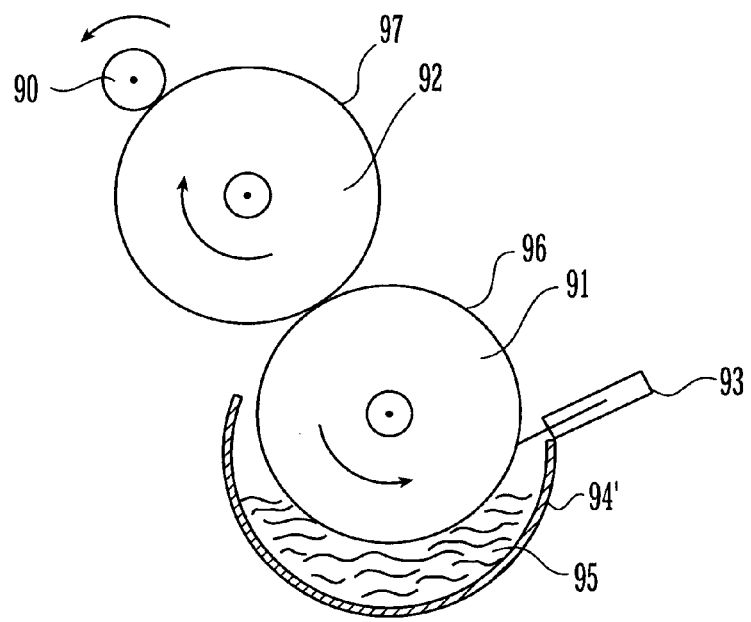

Examples of the systems having two rollers of the present invention are schematically depicted in FIGS. 9A and 9B. In these systems, the first roller 91 is situated relative to the coating material source so that the coating material can be transferred onto the surface of the first roller. Preferably, the first roller 91 rotates in contact with the coating material 95 in the coating material source 94 or 94', and the surface of the first roller 91 is coated with the coating material 95. A doctor blade 93 contacts the coated surface of the first roller 96 and makes the coating material 95 on the roller surface uniform and also removes any excess amount of the coating material 95 from the surface. A second roller 92 is situated relative to the first roller 91 so that the coating material on the first roller's surface 96 can be transferred to the surface of the second roller 97. Preferably, the second roller 92 rotates in contact with the coated surface of the first roller 96. The second roller 92 can rotate in the same or opposite direction as the first roller 91. The second roller 92 is situated relative to the tubular portion of the medical device so that the coating on the second roller's surface 97 can be transferred to the outer surface of the tubular portion 90. Preferably, the outer surface of the tubular portion of the medical device 90 rotates reversely in contact with the surface 97 of the rotating second roller 92, and the coating material on the surface of the second roller 97 is transferred to the outer surface of the tubular portion 90. Inclusion of a second roller 92 enhances the uniformity of the coating material that is applied to the outer surface of the tubular portion 90.

Figure 9C:
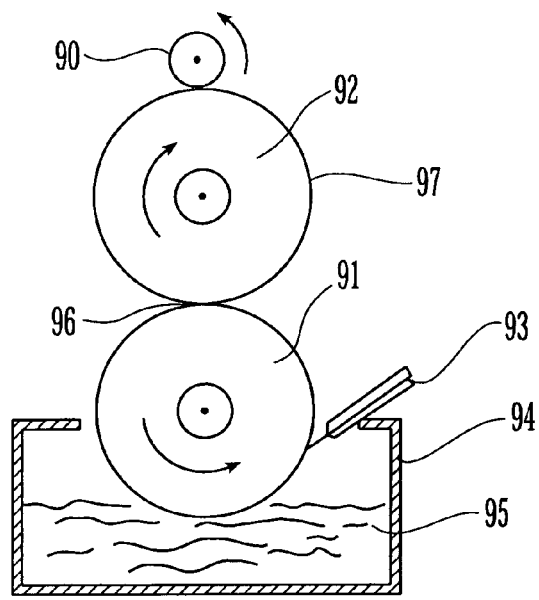
Figure 9D:
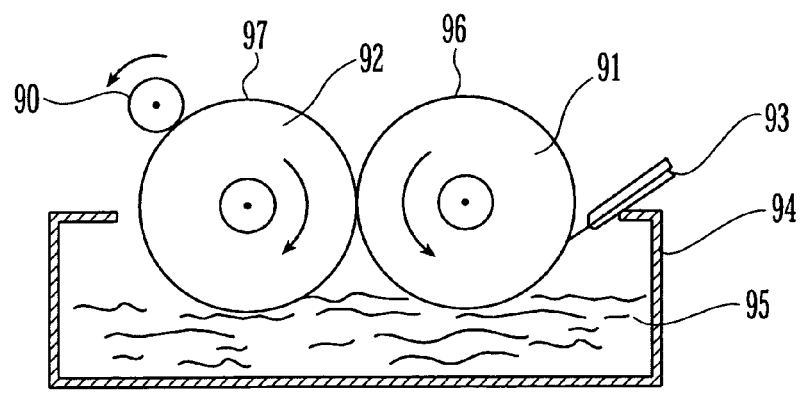

Moreover, the rollers can be placed in various arrangements relative to each other. For example, the rollers can be placed at an angle to each other in FIGS. 9A and 9B. Additionally, the rollers may be placed on top of one another as in FIG. 9C or next to each other as in FIG. 9D.

Figure 9E:
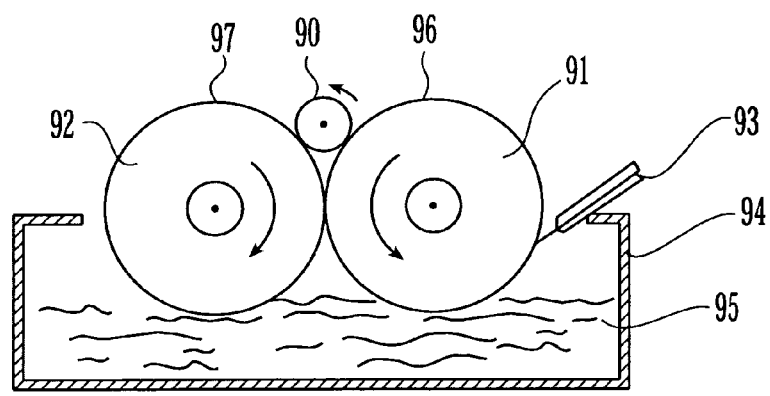

In another embodiment, one of the rollers may be angled with respect to the other roller as shown in FIG. 9E, and the medical device is situated between the rollers. The rollers can turn in the same direction or in opposite directions. The angled roller 92 is used to move the coated device off the rollers. Furthermore, the surface of one of the rollers can be rougher than the surface of the others to cause the stent to rotate. Additionally, three or more rollers can be used in the system and method of the present invention.

Also, a flexible webbing can be included in the system. In particular, a flexible webbing can be tightly extended between two rollers. The webbing can be used to transfer or apply the coating material onto the medical device surface. The use of a flexible webbing to apply the coating material can reduce the chance of damage to the device, which may result from the pressure applied directly to the device surface by a more rigid roller. In certain applications, it may be desirable to press the device into the webbing to force the transfer of the coating material onto the device surface.

Figure 10:
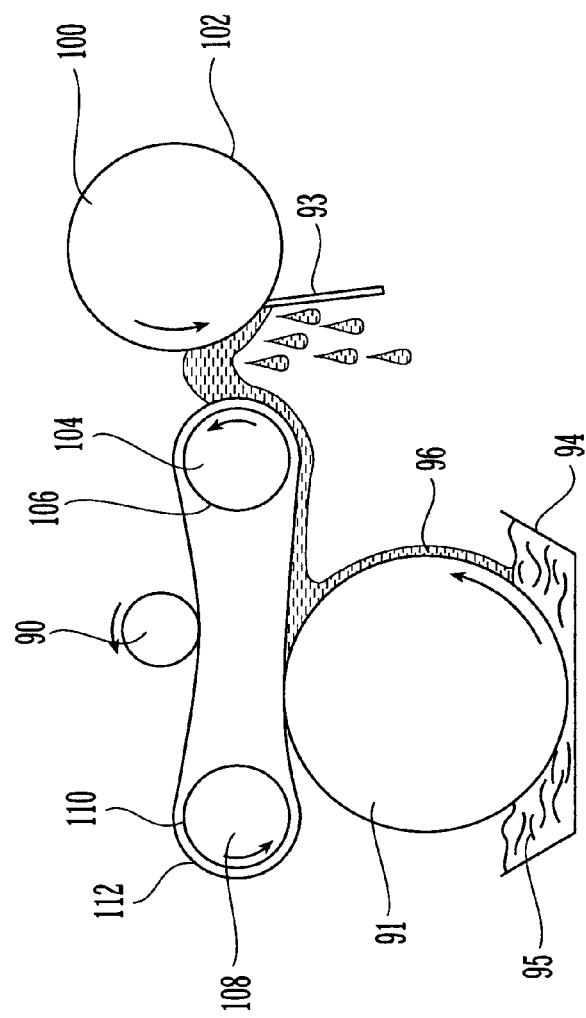
FIG. 10 is a schematic illustration of a coating system comprising rollers and a webbing.

For example, FIG. 10 shows a system of four rollers and a webbing. A first roller 91 having a surface 96 contacts the coating material 95 in coating material source 94. Coating material on the first roller surface 96 is transferred or applied to a flexible webbing 112 by rotating the first roller 91. The webbing is tightly extended between a second roller 104 having a surface 106 and a third roller 108 having a surface 110. The flexible webbing can be made from various materials, including, without limitation, isobutylene, polyurethane or polyurethane rubbers, teflon, textured plastics, nitrite rubbers, and other types of rubbers. Suitable materials for the webbing are selected on the basis of flexure resistance and chemical compatibility with coating materials. For instance, thin, flexible stainless steel belting would also be suitable, and when used with a smooth and corrosion-resistant surface, should also give long, trouble-free performance. A rotating fourth roller 100 having a surface 102 functions as a metering roller to control the thickness or amount of coating material that is applied to the webbing 112. A doctor blade 93 can also be used to control the amount and thickness of the coating material applied to the webbing 112. The coating material on the webbing 112 is applied to the surface of the device 90 as the rollers rotate.

Moreover, in yet another embodiment, a container is not used as part of the coating material source. Instead of placing the coating material in a container, the coating material is measured or metered into a region between two rollers. The space or gap between the rollers controls the amount or thickness of the coating material that may be applied onto an applicator roller, which is used to apply the coating material onto the device surface.

Figure 11:
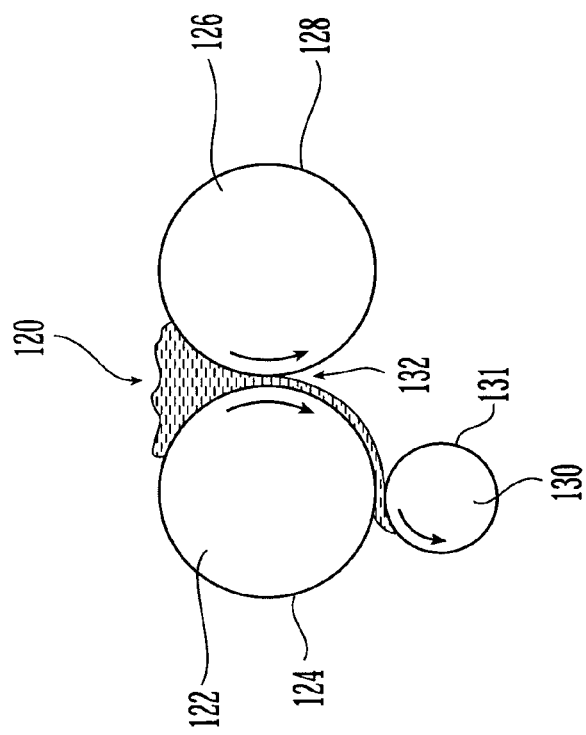
FIG. 11 is a schematic illustration of another coating system comprising rollers.

FIG. 11 shows an example of this embodiment. An amount of coating material 120 is placed between an applicator roller 122 having a surface 124 and a metering roller 126 having a surface 128. A gap or space 132 is located between the applicator roller 122 and metering roller 126. A medical device 130 is situated relative to the applicator roller 122 so that the coating material on the applicator roller 122 can be transferred or applied to the surface 131 of the tubular portion of the medical device 130. In this example, the device 130 is placed below the applicator roller 122. However, the device 130 can be placed in any desired position relative to the applicator roller 122. When the device 130 is placed below the applicator roller 122, gravity assists in the transfer of coating material from the applicator roller 122 to the surface of the device 130.

One skilled in the art can determine an appropriate viscosity of the coating material used for the method of the present invention. Generally, the viscosity of the coating material is slightly greater than that of the coating material used for a spray coating method. The thickness of the coating material transferred to the device surface can be affected by the viscosity as well as other characteristics of the coating material.

Also, appropriate diameters of the rollers can be determined by artisans. The diameter of the first roller may be different from that of the second or other rollers. Preferably, the diameter is from about 100% to about 500% of the diameter of the tubular portion of the device to be coated. The rollers or their surface may be made of a relatively rigid or non-deformable material such as steel or a deformable material such as rubber. One of skill in the art is aware of the appropriate roller materials that can be used in a given application.

Figure 12C:
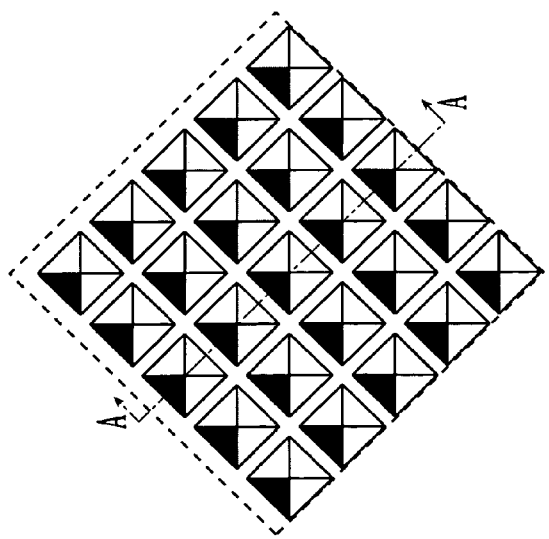
FIGS. 12A, 12B, 12C, 12D, 12E and 12F illustrate patterns of grooves that may appear on the roller surfaces.
Figure 12D:
Figure 12A:
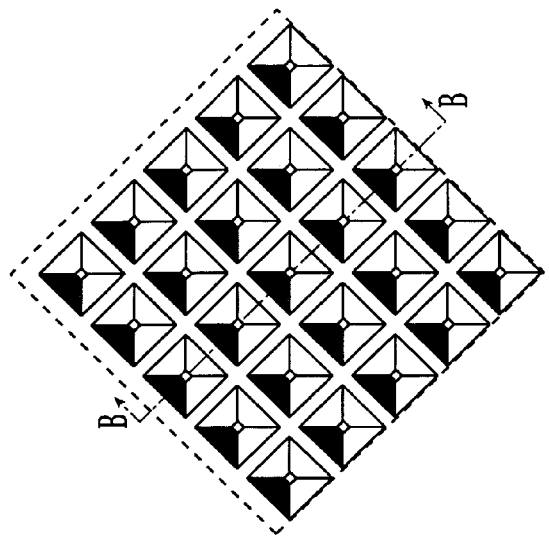
Figure 12B:
Figure 12E:
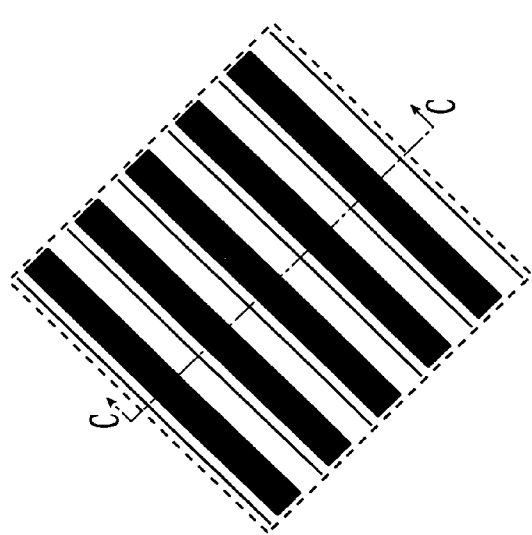
Figure 12F:

Furthermore, the surface of the rollers may have a grooved pattern as in gravure rollers. Such rollers can be used to meter the amount of coating material that is applied to the applicator roller that applies the coating material to the device surface. By selecting the pattern and size of grooves in the roller surface for a particular application and coating material, the desired amount or coverage can be applied to the device surface. FIGS. 12A, 12C and 12E show examples of grooved patterns that can be used. FIG. 12A shows a pyramidal pattern. FIG. 12B shows a cross-section of the pattern of FIG. 12A along line A-A. FIG. 12C shows a truncated pyramidal pattern and FIG. 12D is a cross-section of this pattern along line B-B. Similarly, FIG. 12E shows a pattern, comprising multiple grooves with an obtuse angle and FIG. 12F shows its cross-section having shallow V-shapes along line C-C.

By using the method and system of the present invention, it is possible to obtain a medical device having a tubular portion wherein the outer surface of the tubular portion has a coating but the inner surface does not have the coating. Also, the method and system involving rollers can be used to apply coating material to a surface comprising a plurality of depressions as discussed above. Such method and system can be used to apply the coating material so that the coating material is contained in the depressions but the outermost portion of the surface is substantially free of the coating material. The coating for releasing a biologically active material can be applied only to the outer surface which is directly exposed to body tissue of the patient. Also, another coating material can be applied on the outer surface of the tubular portion of the medical device by repeating the same method to obtain a multilayer coating on the outer surface of the tubular portion.

When more than two coating layers are to be applied on the tubular portion, the method of the present invention can be repeated. After the first coating layer, or underlayer which was applied by the method of the present invention, is dried, then the second coating layer or top layer is applied on the under layer as explained above. Alternatively, another coating method can be used in combination with the coating method of the present invention. Such combination of coating methods are preferable when the first and second coating compositions are different. For instance, the first composition is applied to the outer surface tubular portion of the medical device using the method of the present invention, and the second coating composition is applied to the inner surface using another method, such as a spraying coating. Also, another method can be used first. For example, a drug coating is immobilized on the surface, then another coating composition can be applied using the method of the present invention.

In yet another embodiment, an adhesion protein (e.g., fibronectin) can be applied to a device surface by using a roller. The device surface containing such an adhesion protein can be exposed to a cell suspension. The adhesion protein enhances the coating of the cell suspension onto the device surface.

Figure 13:
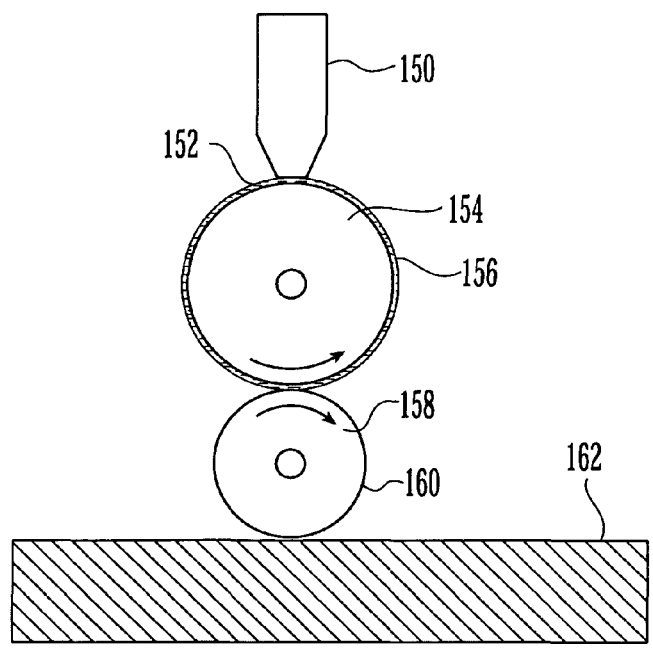
FIG. 13 illustrates a system for coating medical devices involving an adhesion protein and a cell suspension.

FIG. 13 provides an example of such an embodiment. In this system, an adhesion protein applicator 150 applies an adhesion protein 152 to a roller 154 having a surface 156. The roller is situated relative to the medical device so that the adhesion protein applied to the roller 154 can be transferred to the surface 160 of the medical device 158. As the roller 154 rotates, it transfers the adhesion protein 152 that is applied to the roller surface 156 to the outer surface 160 of a medical device 158, such as a stent. The medical device can be mounted on a mandrel (not shown). Furthermore the outer surface of the medical device is exposed to a cell suspension 162 containing for example cells and extracellular matrix materials such as collagen, elastin, proteoglycans or fibronectin. Suitable cells are not limited to particular types. For example, cells that can be used with the invention include, without limitation, fibroblasts, endothelial progenitor cells, endothelial cells, and mysenchymal stem cells. The use of this system results in a multi-laminate of cells and matrix on the stent. Also, the transfer of the adhesion protein from the roller to the outer surface of the device may but need not occur simultaneously with the exposure of the outer surface to the cell suspension.

Figure 14A:
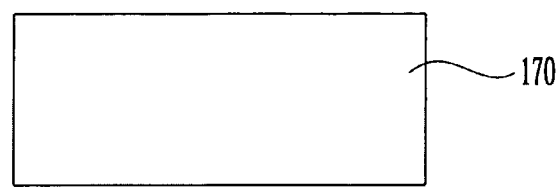
FIGS. 14A, 14B, 14C and 14D illustrate a lithographic coating method.
Figure 14B:
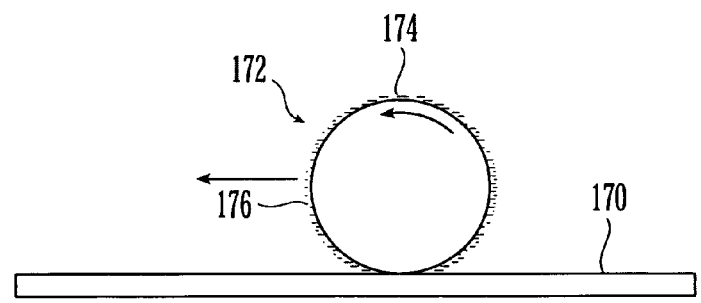

In yet another embodiment, a medical device can be coated by using a lithographic mechanism. This embodiment is depicted in FIGS. 14A, 14B, 14C and 14D. A layer of an unsolidified gel 170 is formed as shown in FIG. 14A. The unsolidified gel 170 can contain biologically active materials such as those discussed above. A medical device 172 whose outer surface 174 is coated with a crosslinking agent 176 is rolled over the unsolidified gel 170 as shown in FIG. 14B. Examples of suitable cross-linking agents include, without limitation, carbodimide, bifunctional aldehydes, calcium chloride, and sulfur. One of skill in the art would be aware of the suitable cross-linking agents that can be used with the unsolidified gel. The device can have openings in the outer surface, such as a stent whose outer surface comprises a plurality of struts.

Figure 14C:
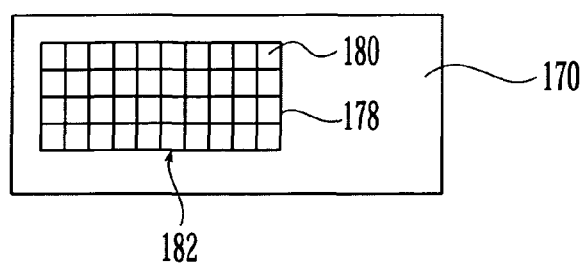
Figure 14D:
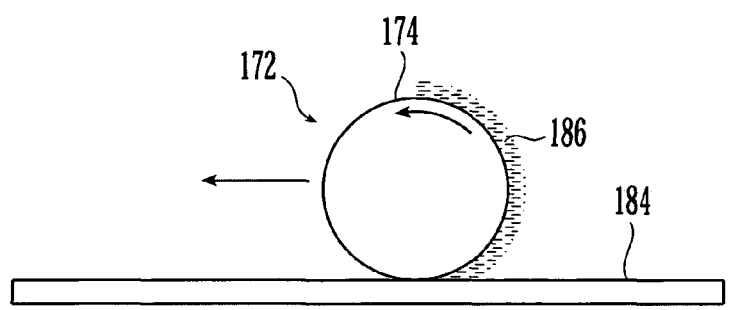

By rolling the crosslinking agent-coated medical device 172 over the unsolidified gel 170, the gel becomes crosslinked only at the areas 178 that contact the rolled device as shown in FIG. 14C. The openings in the outer surface of the device do not include crosslinking agents. These portions of the gel that are exposed to the openings 180 are not crosslinked. The crosslinked portions 178 of the gel 170 form a planar replica 182 of the outer surface of the rolled medical device. This planar replica 178 is then transferred onto the outer surface 174 of the medical device 172 by coating the outer surface 174 with an adhesive. As shown in FIG. 14D, the device 172 with the adhesive-coated outer surface 174 is rolled back over the gel 170 in the same manner that the device was rolled over the gel 170 the first time (see FIG. 14B). This way the outer surface 174 of the medical device 172 will align with the planar replica 178. The adhesive allows a crosslinked layer of gel 184 to form a coating 186 on the outer surface of the medical device 174. Since the crosslinking agents can diffuse a significant distance into gels, a thick coating 186 can result on the outer surface 174.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

What is claimed:

1. A system for coating a stent having a tubular portion with an outer surface, wherein the system comprises:
 a coating material source containing a coating material comprising a solvent and a biologically active material;
 a first roller having a surface;
 a doctor blade in proximity to the first roller surface positioned to remove excess coating material from the first roller surface; and
 a second roller having a surface, wherein:
 the first roller is situated relative to the coating material source so that the coating material in the coating material source is transferred to the first roller surface;
 the first roller and second roller are situated relative to each other so that the first roller transfers the coating material transferred to the first roller surface to the second roller surface, and
 the second roller is situated relative to the tubular portion so that the second roller transfers the coating material transferred to the second roller surface to the outer surface of the tubular portion.

2. The system of claim 1, which further comprises a reservoir that continuously supplies the coating material source with coating material.

3. The system of claim 2, wherein the reservoir is a fermentor containing cells.

4. The system of claim 2, wherein the coating material is circulated between the reservoir and the coating material source.

5. The system of claim 1 wherein the surface of the second roller comprises a plurality of grooves.

6. The system of claim 1, wherein the surface of the second roller is rougher than the surface of the first roller.

7. The system of claim 1, wherein the surface of the first roller contacts the surface of the second roller and the surface of the second roller contacts the outer surface of the tubular portion.

8. The system of claim 1, further comprising a supplemental mechanism for removing excess coating material from the surface of the first roller.

9. The system of claim 8, wherein the supplemental mechanism is at least one of a metering roller or an air knife.

10. The system of claim 1, further comprising an energy source for converting the coating material applied to the outer surface of the tubular portion into a coating.

11. The system of claim 10, wherein the energy source is a heater.

12. The system of claim 10, wherein the energy source is an ultraviolet source.

13. The system of claim 1, wherein the biologically active material comprises a genetic material.

14. The system of claim 1, wherein the biologically active material comprises an antibiotic or an antiproliferative agent.

15. The system of claim 1, wherein said first roller surface comprises an outer surface.

16. The system of claim 1, wherein a distance between the first roller and the second roller is adjustable to control the thickness of the coating material.

* * * * *